(12) United States Patent
Ross

(10) Patent No.: US 6,421,562 B1
(45) Date of Patent: Jul. 16, 2002

(54) ALTERNATIVE TREATMENT OF A NONSURGICALLY TREATABLE INTRACRANIAL OCCLUSION

(76) Inventor: Jesse Ross, 321 E. Shore Rd., Great Neck, NY (US) 11023-2420

( * ) Notice: Subject to any disclaimer, the term of this patent is extended or adjusted under 35 U.S.C. 154(b) by 168 days.

(21) Appl. No.: 09/617,827

(22) Filed: Jul. 17, 2000

(51) Int. Cl.[7] .................................................. A61N 1/00
(52) U.S. Cl. ............................................. 607/2; 607/101
(58) Field of Search ........................... 607/1, 2, 44, 45, 607/46, 71, 72, 100, 101, 154–156

(56) References Cited

U.S. PATENT DOCUMENTS 5,718,721 A  *  2/1998  Ross .............................. 607/2

* cited by examiner

Primary Examiner—George R. Evanisko
Assistant Examiner—Omar Khan
(74) Attorney, Agent, or Firm—Myron Amer P.C.

(57) ABSTRACT

An alternative treatment of a nonsurgically treatable intracranial occlusion using twenty minute duration sessions of exposure to radio-frequency pulsed high-peak power electromagnetic energy until there is no longer any manifesting of conditions each or combination of episodic dizzy spells and sudden hemiplegia.

1 Claim, 1 Drawing Sheet

ALTERNATIVE TREATMENT OF A NONSURGICALLY TREATABLE INTRACRANIAL OCCLUSION

BACKGROUND OF THE INVENTION

The present invention relates generally to the use in the treatment of an intracranial occlusion of radio-frequency pulsed high frequency electromagnetic energy to effectively stimulate the endothelial cells of the capillaries and cell membranes of the vascular wall to obviate insufficiency of arterial blood flow in the brain. Vascular obstruction or vascular rupture which can cause embolic, ischemic, or thrombotic stroke resulting in paralysis can thus be avoided.

DESCRIPTION OF THE RELATED ART

It is known from medical literature that gradual mental deterioration, episodic weak or dizzy spells, or sudden complete hemiplegia may occur as a result of a variety of causes, and that occlusive complications account for many of these problems. In approximately one-third of cases, the occlusion is of the extracranial vessels and if not remedied is responsible for either the major stroke or, more frequently, the recurrent "little strokes" or ischemic episodes. Surgery can be an available and effective remedy. However, in two-thirds of cases occlusions are intracranial and thus not usually amenable to surgical correction.

BRIEF SUMMARY OF THE INVENTION

This invention is concerned with intracranial occlusions and proposes an effective nonsurgical remedy. Underlying the present invention is the recognition of certain physical factors involved in the activation of the fibrinolysin system. When, for instance, the activation is mediated by way of the neural pathways to the peripheral areas of the vascular system, an electrical factor is generated by the physical stress. This phenomenon of producing electron currents in living cells and tissue by physical stress can be explained by the effects of "piezoelectric resonance" in the cell structure, that is, the characteristic which cells have of discharging electrons when exposed to pulsed stress on their membrane and intracellular macromolecular content. These electron currents, if induced by a pulsed electromagnetic field in the radio-frequency region, can result locally in the same physiochemical response as the pulsed neural stimulation.

More particularly, what is proposed is stimulation through the piezoelectric resonant effect of the vascular cell membranes and the macromolecular content of the thrombus formation that is, by radiation of radio-frequency pulsed high frequency electromagnetic energy. This is an athermic method of stimulating the endothelial cells of the capillaries and cell membranes of the vascular wall, which releases the activator of plasminogen and stimulates the activator molecular enzymes within the thrombus. This method of therapy can be administered without side effects or contraindications in all forms of strokes.

BRIEF DESCRIPTION OF THE DRAWINGS

The description of the invention which follows, together with the accompanying drawings should not be construed as limiting the invention to the examples shown and described, because those skilled in the art to which this invention appertains will be able to devise other forms thereof within the ambit of the appended claims.

DESCRIPTION OF THE PREFERRED AND ILLUSTRATED EMBODIMENTS OF THE INVENTION

Figure 1:
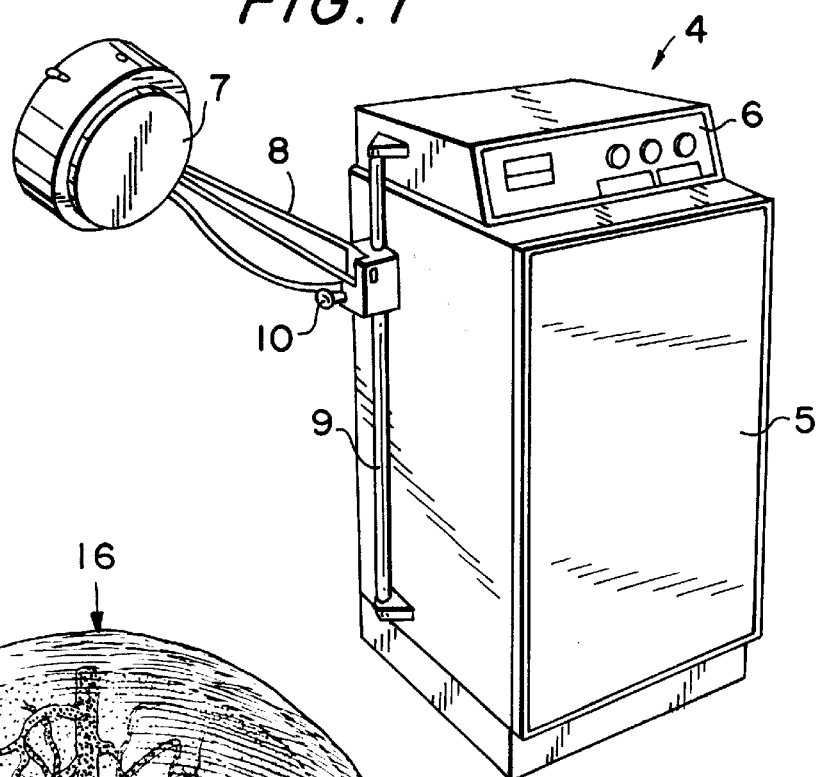
FIG. 1 is a perspective view of an apparatus for generating an electromagnetic field for practicing the within inventive method.
Figure 2:
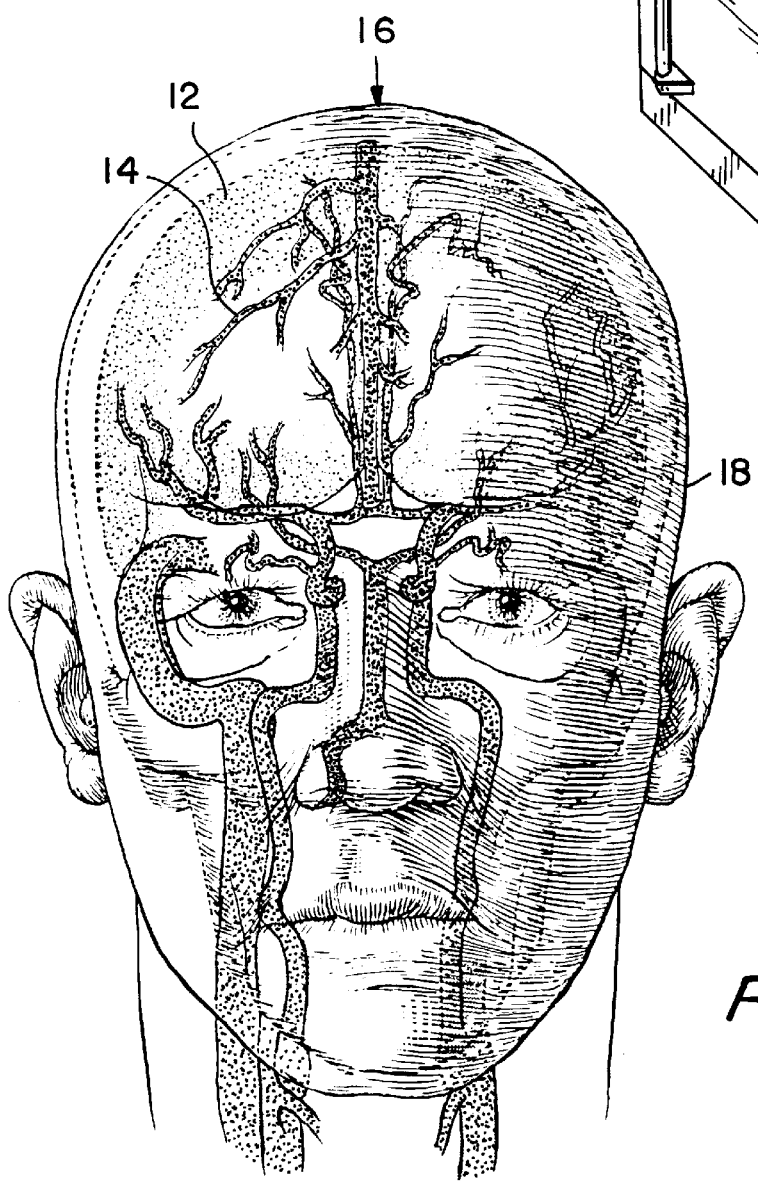
FIG. 2 is a front elevational view of a graphic of a treatment site of the electromagnetic field.

Shown in FIG. 1 is an athermapeutic apparatus for the generation of pulsed high frequency oscillations to which a patient is subjected, of a type which is now well known to the art wherein the pulse frequency and duration is of such nature that the total time period during which electrical energy is actually induced into the body of a patient is so short that despite the comparatively high instantaneous energy level of the pulsed power, it is unaccompanied by heat generation because the time for heat dissipation is many times longer than the heat accumulation. The athermapeutic apparatus 4 as therein shown comprises a cabinet 5 provided with a control panel 6, for regulating the pulse repetition rate and pulse duration, timer setting, etc., and having a treatment head 7. Such treatment head is carried by an arm 8 to which it is pivotally connected, and with the arm in turn being reciprocally and axially movable on a tubular support 9 and secured in any desired adjusted position relative to the support 9 by a locking screw 10.

Diapulse Treatment of Intracranial Occlusions

The treatment is practiced with an athermapeutic apparatus 4 commercially available from Diapulse Corporation of America, located at 321 East Shore Road, Great Neck, N.Y., and in the trade its mechanism of action is known as Diapulse Therapy. The apparatus is illustrated and described in my U.S. Pat. 5,718,721 entitled "Method of Relieving Migraine Headache Pain" issued on Feb. 17, 1998 which patent, by this reference, is incorporated herein as if fully set forth in this specification. More particularly, it provides adjunctive therapy with pulsed high frequency electromagnetic energy (Diapulse) and consists of exposure provided by the adjacent positioning of the treatment head 7 at a control panel 6 setting of 4–6, for 20 minute sessions each over the side 12 of the involvement 14 in the brain 16 and vertically downward over the vertex of the head 18.

The operating mode which in practice has resulted in successful remedy of the adverse effect of intracranial occlusions is an electromagnetic field having the following specific parameters:

1. A frequency of 27.12 megahertz (11 meter band);
2. A pulse repetition rate of 80 to 600 pulses per second;
3. A pulse width of 65 microseconds;
4. A power range, per pulse, of between 293 and 975 watts;
5. A duty cycle between ½ of 1% to 3.9%; and
6. A square pulse, with a rise and fall time less than 1%.

An exemplary account of the described diapulse treatment is reported below: "A 79 year old white female developed right side cerebral vascular accident with coma eight days duration and left side hemiplegia. Administered treatment and had complete symptomatic recovery in 14 days. Expired three weeks later from pneumonia. Necropsy: Brain wt. 980 grams. There is a depression at the right frontopariototemporal junction with the cortex approximately 1.5×0.5 cm. There was coronal sections through the cerebral hemispheres revealing no evidence of underlying lesions. However, the cerebral vessels are all focally thickened and tortuous, particularly those of the circle of Willis and the basilar artery. The pons appear mottled, but there is no evidence of a definite lesion. The cerebellum, midbrain and medulla are negative."

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. An alternative treatment of a nonsurgically treatable intracranial occlusion manifesting conditions each or a combination of episodic dizzy spells and sudden hemiplegia comprising the steps of:

a. selecting as a site of treatment the side of the brain of intracranial occlusion involvement and vertically downward over the vertex of the head;

b. exposing this treatment site for a selected number of twenty minute duration sessions with an electromagnetic field of (1) a frequency of 27.12 megahertz, (2) a pulse repetition rate of 80 to 600 pulses per second, (3) a pulse width of 65 microseconds, (4) a power range, per pulse, of between 293 and 975 watts, (5) a duty cycle between ½ of 1% to 3.9%, and (6) a square pulse, with a rise and fall time less than 1%; and c. repeating said sessions of step b to an extent that obviates manifesting of conditions each or combinations of episodic dizzy spells and sudden hemiplegia;

whereby the treatment is provided to a patient without surgery and without the occurrence of said intracranial occlusion as a lesion.

* * * * *